(12) United States Patent
Garaci et al.

(10) Patent No.: US 8,431,617 B2
(45) Date of Patent: Apr. 30, 2013

(54) USE OF RESVERATROL FOR THE PREPARATION OF A MEDICAMENT USEFUL FOR THE TREATMENT OF INFLUENZA VIRUS INFECTIONS

(75) Inventors: Enrico Garaci, Rome (IT); Anna Teresa Palamara, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 1653 days.

(21) Appl. No.: 10/533,942

(22) PCT Filed: Oct. 14, 2003

(86) PCT No.: PCT/IT03/00626
§ 371 (c)(1),
(2), (4) Date: May 4, 2005

(87) PCT Pub. No.: WO2004/041260
PCT Pub. Date: May 21, 2004

(65) Prior Publication Data
US 2005/0239906 A1    Oct. 27, 2005

(30) Foreign Application Priority Data

Nov. 6, 2002 (IT) .............................. RM2002A0562

(51) Int. Cl.
*A61K 31/05* (2006.01)
(52) U.S. Cl.
USPC ........................................................ 514/733
(58) Field of Classification Search .................... 514/733
See application file for complete search history.

(56) References Cited

U.S. PATENT DOCUMENTS 6,479,466 B1 * 11/2002 Redfield et al. ................. 514/45

FOREIGN PATENT DOCUMENTS

| WO | WO 99/56737 | 11/1999 |
| WO | WO 01/08671 A2 | 2/2001 |
| WO | WO 01/12228 A2 | 2/2001 |

OTHER PUBLICATIONS

Heredia A, Davis C, and Redfield R, "Synergistic inhibition of HIV-1 in activated and resting peripheral blood mononuclear cells, monocyte-derived macrophages, and selected drug-resistant isolates with nucleoside analogues combined with a natural product, resveratrol," Journal of Acquired Immune Deficiency Syndromes, Nov. 2000, 25(3), 246-255.*
Kurokawa M, Ochiai H, Nakajima K, and Niwayama S, "Inhibitory effect of protein kinase C inhibitor on the replication of influenza type A virus," Journal of General Virology, Sep. 1990, 71(9), 2149-2155.*
Pätzold S, Schneider J, Rudolph C, Marmé D, and Schächtele C, "Novel indolocarbazole protein kinase C inhibitors prevent reactivation of HIV-1 in latently infected cells," Antiviral Research, Dec. 1993, 22(4), 273-283.*
Stewart JR, Ward NE, Ioannides CG, and O'Brian CA, "Resveratrol preferentially inhibits protein kinase C-catalyzed phosphorylation of a cofactor-independent, arginine-rich protein substrate by a novel mechanism," Biochemistry, Oct. 1999, 38(40) 13244-13251.*
Root CN, Wills EG, McNair LL, and Whittaker GR, "Entry of influenza viruses into cells is inhibited by a highly specific protein kinase C inhibitor," Journal of General Virology, Nov. 2000, 81(Pt 11), 2697-2705.*
International Search Report of PCT/IT03/00626, mailed Mar. 3, 2004.

* cited by examiner

*Primary Examiner* — Paul Zarek
(74) *Attorney, Agent, or Firm* — Lucas & Mercanti, LLP

(57) ABSTRACT

The use of resveratrol is described fir the preparation of a medicament for the treatment of influenza. Said medicament exerts itself in therapeutic activity through inhibition of viral replication.

12 Claims, 12 Drawing Sheets

Effect of resveratrol on influenza pr8 viral replication in MDCK cells

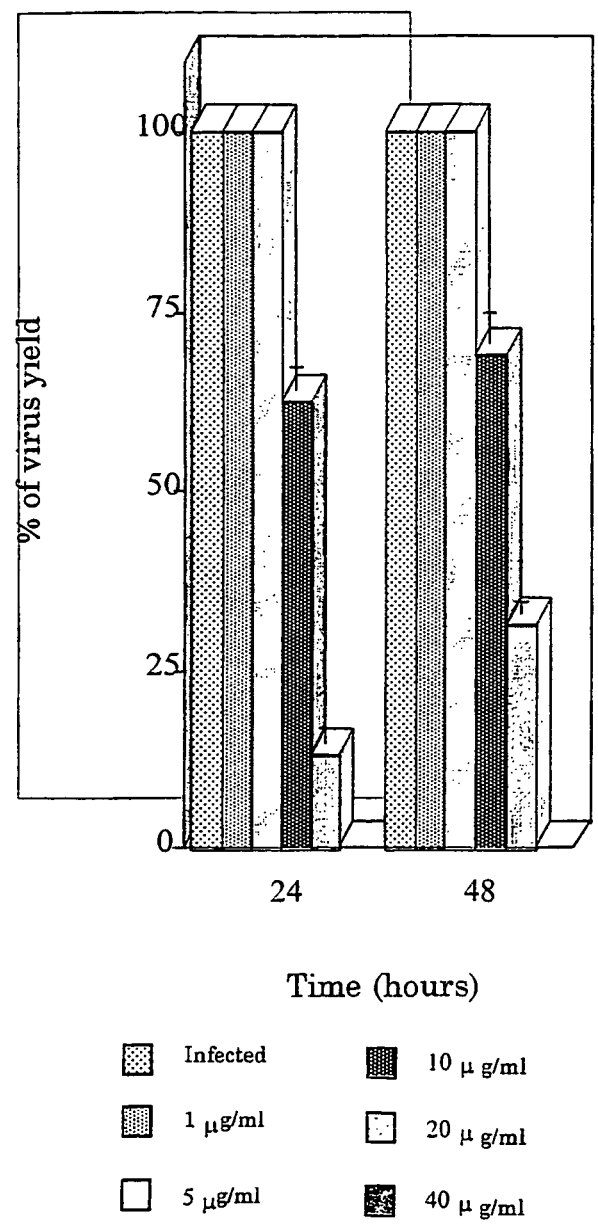
Figure 1 (continues)
C) Pre-post infection

Effect of Resveratrol on confluent monolayer of uninfected MDCK cells.

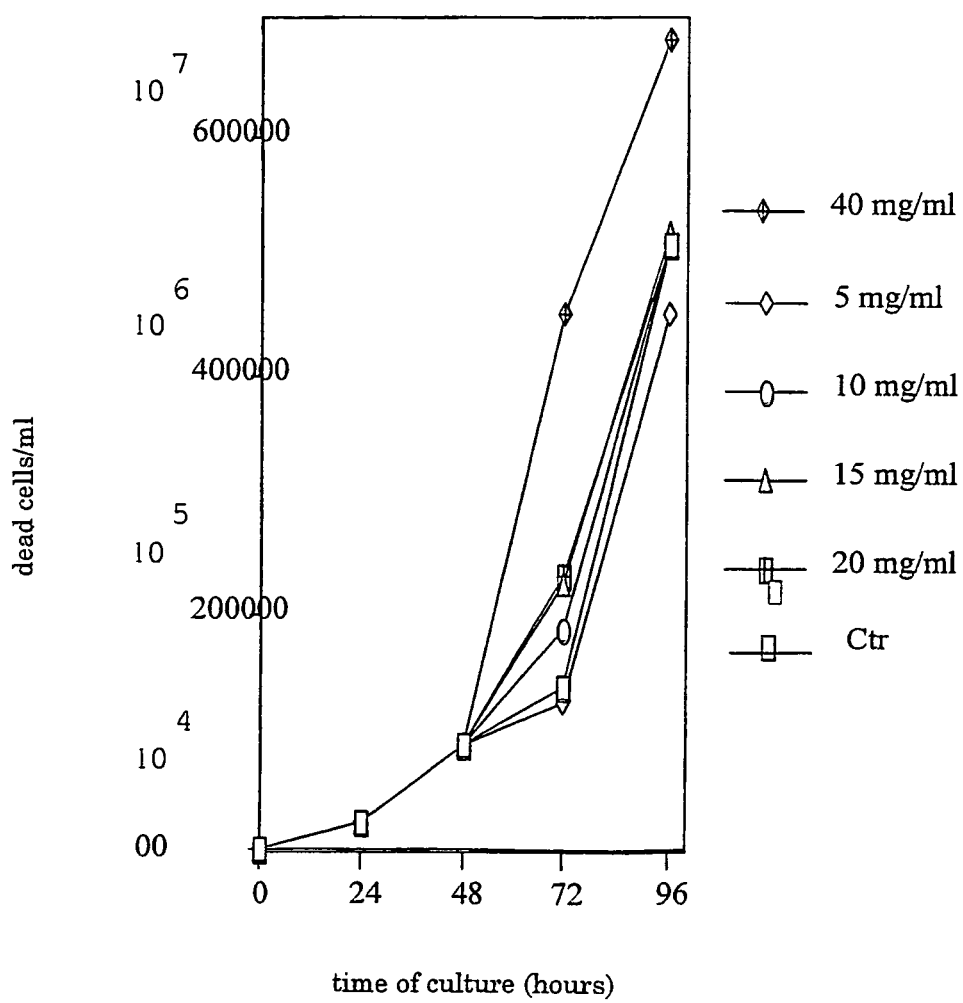
Figure 2B (continues)

Characterization of antiviral activity of Resveratrol

Characterization of antiviral activity of resveratrol

Characterization of antiviral activity of Resveratrol

Apoptosis in Resveratrol-treated MDCK cells

Correlation of antiviral effect of resveratrol with intracellular redox state

Effect of Resveratrol on synthesis of influenza a pr8 viral proteins

RT-PCR for mRNA to late viral proteins

Resveratrol (mg/ml)

Effect of Resveratrol administrated after influenza pr8 viral infection on in vivo

USE OF RESVERATROL FOR THE PREPARATION OF A MEDICAMENT USEFUL FOR THE TREATMENT OF INFLUENZA VIRUS INFECTIONS This application is the U.S. national phase of international application PCT/IT2003/000626 filed 14 Oct. 2003 which designated the U.S. and claims priority of IT RM2002A000562, dated 6 Nov. 2002, the entire contents of each of which are hereby incorporated by reference.

The invention described herein relates to the use of resveratrol as an active ingredient in the preperation of a medicament for treating influenza virus infections.

BACKGROUND OF THE INVENTION

Resveratrol, i.e, 3,4,5-trihydroxystilbene, has been intensively studied recently, in relation to the known beneficial properties of red wine, of which it is one of the fundamental ingredients (*Life Sci.*, 71, 2145-52, 2002).

Resveratrol is located in the skins of black grapes in amounts ranging from 50 to 100 µg/gram and its concentration in red wine ranges from 1.5 to 3 mg/l.

Numerous studies have demonstrated an anticarcinogenic activity of resveratrol, the mechanisms of action of which can be subdivided as follows: inhibition of activation of transcription factor NF-kB, capable of regulating the expression of various genes involved in inflammatory and carcinogenic processes (*Lancet*, 341, 1103-1104, 1993; *Science*, 275, 218-220, 1997; *Proc. Natl. Acad. Sc.*, 94, 14138-14143, 1997; *Life Science*, 61, 2103-2110, 1997; *Brit. J. Pharin.*, 126, 673-680, 1999; *J. Imm.*, 164, 6509-6519, 2000); inhibition of various proteins, including protein kinase C (*Bioch.*, 38, 13244-13251, 1999), ribonucleotide reductase (*FEBS Lett.*, 421, 277-279, 1998) and cyclo-oxygenase-2 (COX-2) in mammalian epithelial cells (*Ann. N.Y. Acad. Sci*, 889, 214-223, 1999; *Carcinog.*, 21, 959-963, 2000); activation of caspases 2, 3, 6 and 9 (*FASEB J.*, 1613-1615, 2000) and modulation of the gene p53, which is a known tumour suppressor (*Cancer Research*, 59, 5892-5895, 1999; *Clin. Bioch.*, 34, 415-420, 2001).

Among the beneficial actions of resveratrol we should also mention its antioxidant activity, suggested by the above-mentioned ability to counteract the damaging effects produced by various substances and/or conditions that cause intracellular oxidative stress (*Free Radic. Res.*, 33, 105-114, 2000).

Resveratrol can induce vascular relaxation by means of production of nitric oxide at the vascular endothelial level (*Cancer Res.*, 59, 2596-01, 1999), inhibit the synthesis of thromboxane in platelets (*Clin. Chim. Acta*, 235, 207-219, 1995; *Int. J. Tissue React.*, 17, 1-3, 1995), and of leukotrienes in neutrophils and prevent the oxidation and aggregation of low-density lipoproteins (LDL) (*Lancet*, 341, 1103-1104, 1993; *Life Sci.*, 64, 2511-2521, 1999).

Recently, an inhibitory activity of resveratrol against the Herpes Simplex DNA virus has been demonstrated (*Antiv. Res.*, 43, 145-155, 1999) on the basis of in-viutro experimental systems.

Data obtained by the present authors and by other research teams have revealed that many antioxidant substances are capable of inhibiting the replication of the parainfluenza Sendai virus (SV) type 1, of the Herpes Simplex 1 virus (HSV-1) and of the acquired immunodeficiency virus (HIV) in vitro (*AIDS Res. Hum. Retoviruses*, 1997: 1537-1541; *Biochem. Biophys. Res. Communt.*, 1992; 188, 1090-1096; *Antivir. Res.*, 1995, 27, 237.253). The antiviral efficacy of antioxidant substances has also been demonstrated in a murine AIDS (MAIDS) model, as well as in HSV1 keratitis (*AIDS Res. Hum. Retroviruses*, 1996: 12, 1373-1381: *Exp. Eye. Res.*, 200: 70, 215-220).

Influenza is an epidemiological problem of worldwide proportions with serious public health problems as a result and with major health-care economic repercussions. The virus responsible for influenza is widespread and highly infectious. Unfortunately, the therapies currently available are still not fully effective and often lead to the selection of resistant viral strains (*Fields, cap*47, 1533-79, 2001) and, what is more, the vaccination campaigns, in addition to the disadvantages inherent in vaccine-based prevention, do not as yet provide satisfactory cover owing to the extreme antigenic variability of the virus (*Fields, cap*47, 1533-79, 2001).

Among the various strategies for attacking viral replication, recent studies (*J. of Virol.*, 74, 1781-1786, 2000) have reported the important role of protein M1 in the transportation of specific virus ribonucleoproteins to the cytoplasm. This appears to be a fundamental stage in the replication cycle of the virus, so much so that inhibition of viral replication can be pursued through retention of the nucleoprotein in the nucleus of the infected cell due to the inhibited synthesis of protein M. This phenomenon may be attributable to inhibition of cell proteins with a kinase function. In fact, it has recently been demonstrated that inhibition of the kinases causes retention of the NP of the cell nucleus (*Nature Cell. Biol.*, 3, 301-5, 2001; *J. of Virol.*, 74, 1781-86, 2000), together with a potent inhibitory action against replication of the influenza virus.

GSH is known to be the main antioxidant in the cellular redox system and has been associated with the replication of various viruses. In fact, previous studies conducted by the present inventors have demonstrated that during viral infection it is possible to observe a reduction in GSH levels as a result of the infection itself (Rotilio et al., "*Oxidative stress on cell activation in viral infection*", 143-53, 1993; *Palainara et al., Antiviral Research*, 27, 237-53, 1995).

Aberrant regulation of the known mechanism of apoptosis is the underlying factor responsible for numerous human diseases, such as a number of autoimmune, infectious or neurological diseases such as AIDS and cancer.

In previous studies, it has been described that resveratrol permits the elimination of tumour cells through induction of apoptosis of the cells. Recently, studies conducted by Tinhofer I. et al. (*FASEB J.*, 18, 1613-15, 2001) have revealed that the first events of apoptosis induced by resveratrol are characterised by alteration of the mitochondrial membrane potential ($\Delta\Phi m$), by the release of reactive oxygen species (ROS) and by activation of caspases 2, 3, 6 and 9. It is also known that the influenza virus induces apoptosis in various percentages, according to the viral strain and the multiplicity of infection.

SUMMARY OF THE INVENTION

It has now been found that resveratrol exerts an inhibitory action on influenza virus replication. In an entirely surprising manner, it has also been found that resveratrol exerts its inhibitory action on influenza virus replication not through the expected antioxidant activity, but through a particular mechanism of inhibition of protein kinase C, a cell enzyme that plays a major role in the influenza virus replication process. The main advantage afforded by the use of resveratrol would therefore consist in its ability to attack the virus indirectly, i.e. by interfering with a functional cell structure of the virus, rather than with the viral particle in itself. This type of approach might therefore lead to inhibition of the virus, avoiding the occurrence of the phenomenon of resistance to the most common antiviral drugs.

Accordingly, one object of the present invention is the use of resveratrol for the preparation of a medicament useful for the prevention and/or treatment of influenza virus infections. In a preferred application of the present invention, resveratrol is used against the human influenza virus. In a broader application of the invention, its objectives also include the use of resveratrol for the preparation of a medicament useful for the treatment of influenza virus infections in the veterinary field.

The present invention will now be illustrated in detail, also with the aid of examples and figures, where:

DETAILED DESCRIPTION OF THE INVENTION

For the purposes of illustrating the efficacy of the present invention, in-vitro studies have been conducted using influenza virus A/PR8/34, subtype H1N1 (hereinafter referred to in brief as virus PR8). This strain was used purely by way of an example, it being understood that the present invention is applicable to the influenza virus in the general sense of the term.

Materials and Methods

Resveratrol is a product which is commonly available on the market or which can be obtained using the known methods reported in the literature. The substance was used dissolved in DMSO (80 mg/ml). The concentrations used for the experiments were obtained by means of successive dilutions in RPMI 1640. All the control samples were treated with DMSO at the same doses used to dissolve the resveratrol. At these concentrations the DMSO produced no toxic effects on the cells.

Cell Cultures

For the study of influenza virus replication MDCK cells (dog kidney epithelial cells) were used. The cells were cultured in T-25 vials or in 6- and 24-well Libno plates in RPMI culture medium added with L-glutamine, penicillin-streptomycin and 10% foetal calf serum (FCS) and maintained at 37° C. in a 5% $CO_2$ atmosphere. The confluent cell monolayers were detached with a 0.25% trypsin solution, centrifuged and reseeded in fresh medium. The cell count was done using a haemocytometer and cell viability was determined by means of exclusion with Trypan Blue viability staining (0.02%).

Production of the Virus

The virus was produced by means of inoculation of a viral suspension suitably diluted in the 10-day embryonated chicken egg allantoid cavity. After incubating the eggs at 37° C. for 72 hours, the allantoid fluid containing the newly formed viral particles was clarified by centrifuging at +4° C. and stored at −80° C.

Titration of the Virus

The titration of the virus was done using the haemoagglutinin technique which is based on the ability, peculiar to this virus, to agglutinate blood cells.

The undiluted virus in the allantoid fluid was titrated by scalar dilution with phosphate buffer saline (PBS) in 96-well plates, to which a 0.5% suspension of human blood cells of the 0 Rh+ group was later added. The plates were then left at ambient temperature long enough for the haemoagglutination reaction to take place. The viral titre of the sample, expressed in haemagglutinating units (HAU), was represented by the last dilution giving rise to complete haemoagglutination. The release of virus on the part of infected cells was evaluated with the same procedure on the supernatants of the infected samples that were drawn 24 and 48 h after infection.

Viral Infection

Figure 1:
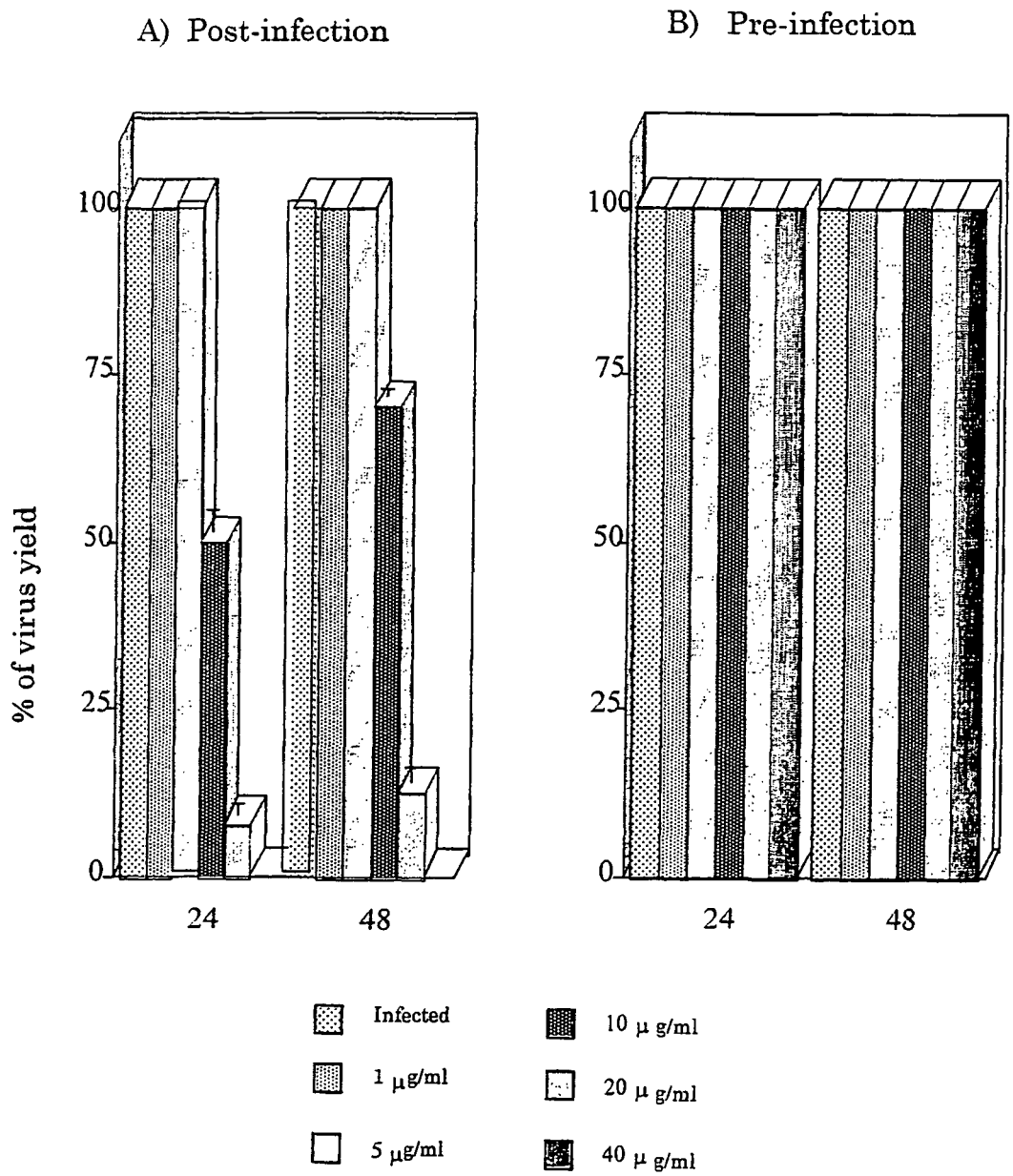
FIG. 1 illustrates the effect of resveratrol on the replication of the influenza virus PR8 in MDCK cells, and, to be precise, in FIG. 1A in the case of post-infection administration, in FIG. 1B in the case of pre-infection administration, and in FIG. 1C in the case of pre- and post-infection administration.
Figure 2A:
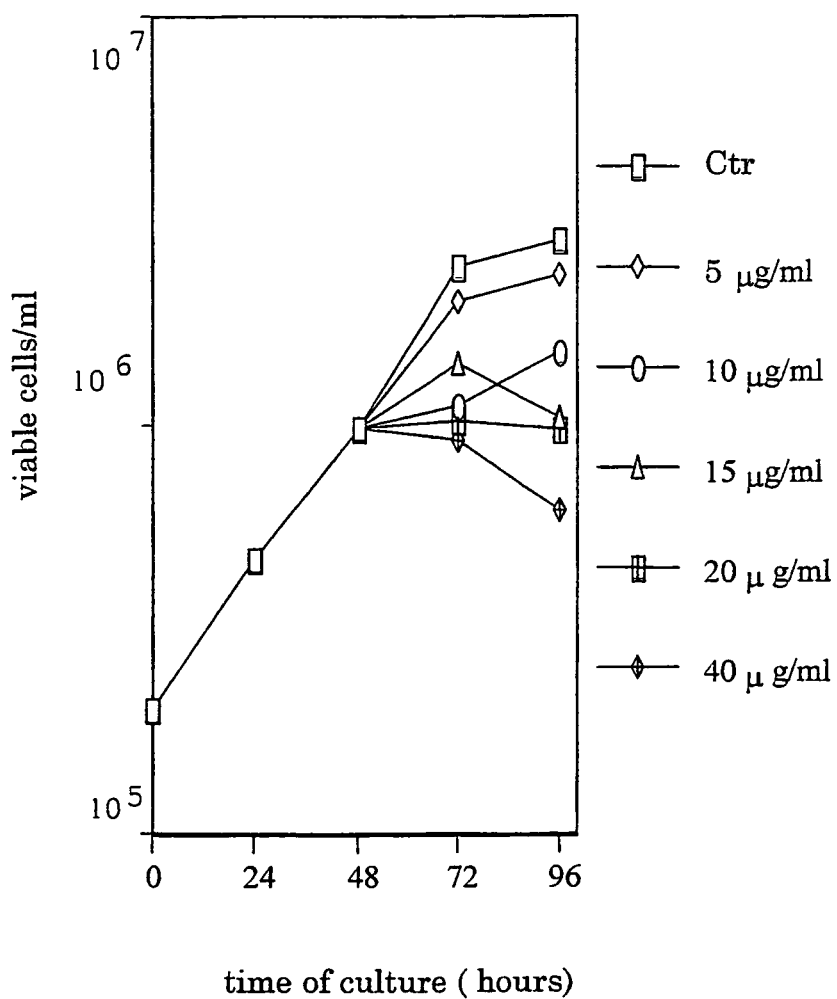
FIG. 2 illustrates the effect of resveratrol on confluent monolayers of uninfected MDCK cells, and, to be precise, the number of viable cells.

The confluent monolayers of MDCK cells were washed with PBS and infected with the virus (0.2 multiplicity of infection [m.o.i.]). In particular, the virus was suitably diluted in RPMI without FCS and added to the cell in the minimum volume. After 1 hour of incubation at 37° C. (period of adsorption of the virus), the inoculum was removed and the monolayers, after washing with PBS to remove the excess unadsorbed virus, were maintained in fresh medium containing 2% FCS. Resveratrol was added at various concentrations (1, 5, 10, 15, 20 and 40 µg/ml), according to the following treatment schedules: a) 24 h before infection (pre-); b) immediately after adsorption of the virus to the infection cells (post-); and c) 24 h before and immediately after adsorption of the virus to the infection cells (pre-post). In all cases, the substance was left to incubate for the entire duration of the experiment. 24 and 48 h after infection, the virus released in the supernatant was titrated by evaluation of the haemoagglutinating units. As shown in FIG. 1, resveratrol added post-infection inhibited viral replication in a dose-dependent manner. At the concentration of 20 µg/ml, the viral titre was reduced by 87% compared to infected and untreated controls, without any toxic effects on the uninfected cells being detected. For the purposes of determining the possible degree of toxicity on the MDCK cells, the latter were treated with resveratrol after the confluence of the monolayer, at various concentrations (5, 10, 15, 20 and 40 µg/ml). The results obtained demonstrate that at the doses that caused significant inhibition of the influenza virus (10-20 µg/ml), a slight reduction in cell number was observed, probably due to a slowing-down of cell proliferation (FIG. 2A). At these doses, however, no morphological alterations of the cells were observed. At the concentration of 40 µg/ml, at which viral replication was completely blocked, however, toxic effects were observed with an increase in cell mortality (FIG. 2B). On the basis of this result, in the following experiments the dose of 20 µg/ml was used, which produced maximal antiviral activity without side effects.

Characterisation of Antiviral Activity

Figure 3:
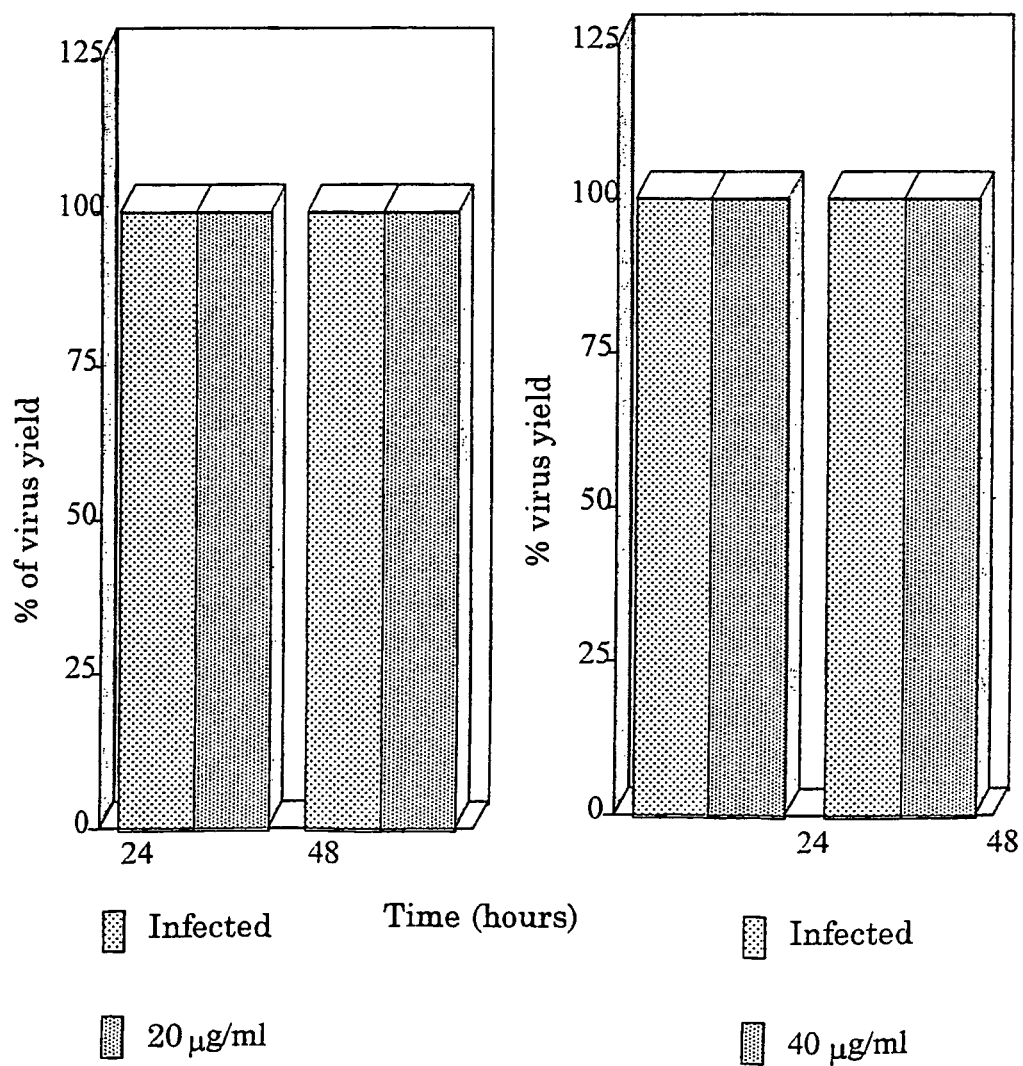
FIG. 3 illustrates the characterisation of the antiviral activity of resveratrol, and, to be precise, in FIG. 3A the treatment during viral adsorption and in FIG. 3B the effect on the viral particles.
Figure 4A:
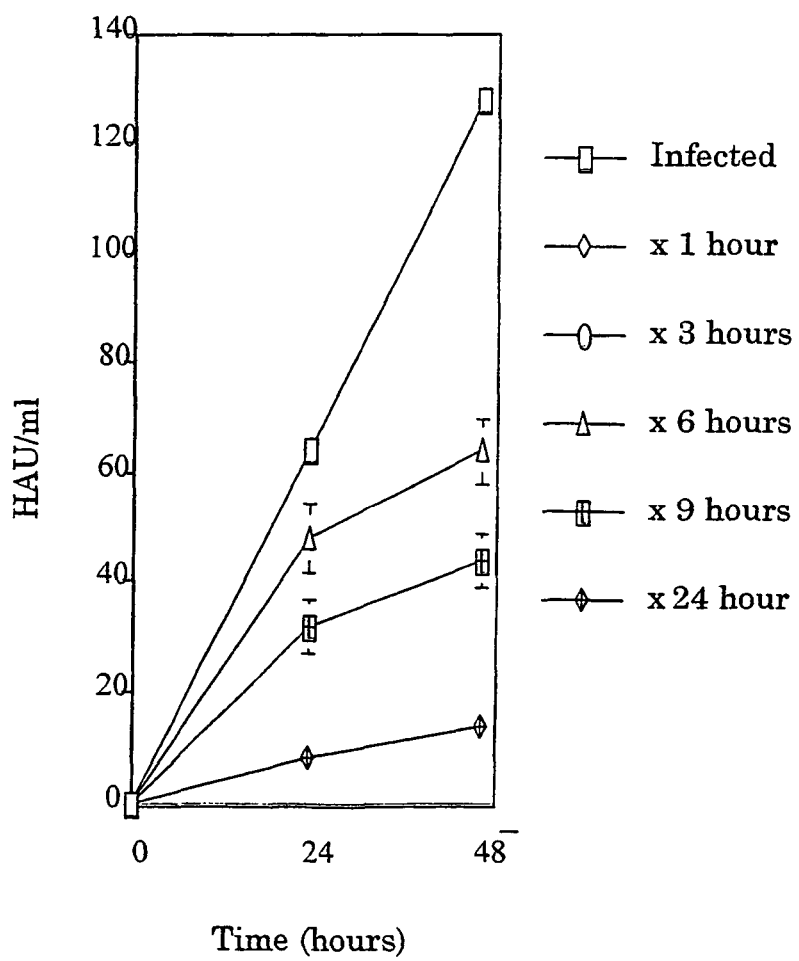
FIG. 4 illustrates the characterisation of the antiviral activity of resveratrol, and, to be precise, in FIG. 4A in the case of administration immediately after the infection and removal at different times, and, in FIG. 4B, in the case of addition at different times in relation to infection.
Figure 4B:
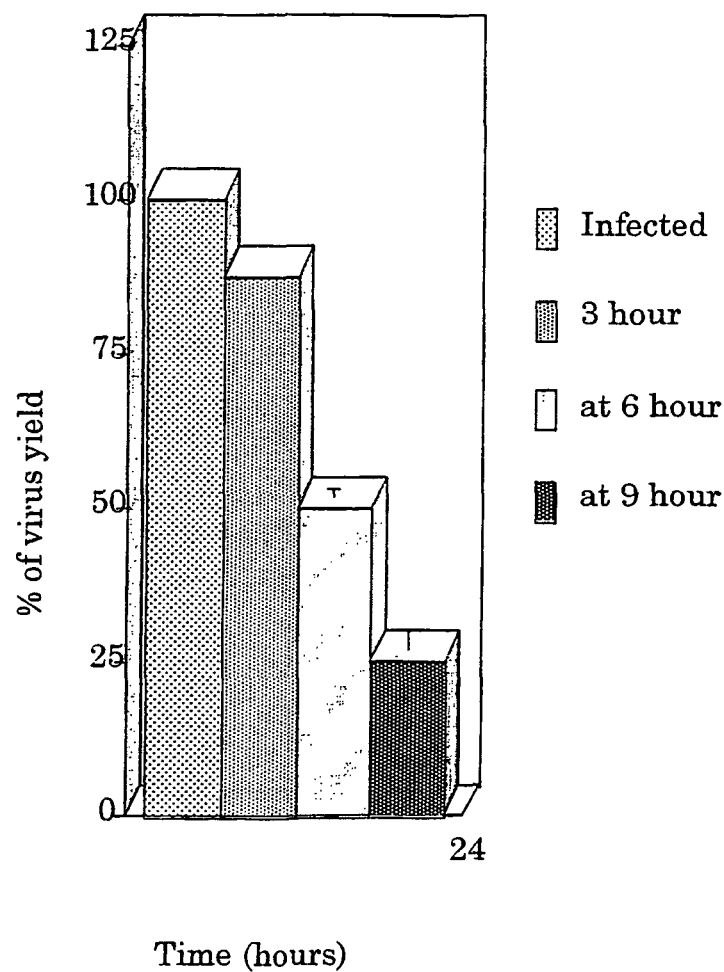

With the aim of identifying the phases of the viral replication cycle controlled by resveratrol, the substance was added according to different treatment schedules in relation to the various phases of the life cycle of the virus. In the first phase, for the purposes of assessing whether resveratrol interferes with entry of the virus into the cells, the substance was added at a concentration of 20 μg/ml exclusively during the viral adsorption phase (for one hour at 37° C.) and then removed. Measurement of viral replication after 24 h proved comparable to the replication obtained in the control cells, thus demonstrating that entry of the virus was not inhibited by the drug (FIG. 3). Moreover, to assess whether resveratrol was capable of directly inactivating the virus, the latter was incubated with the substance at a concentration of 40 μg/ml for one hour at 37° C. Later, the virus thus treated was diluted 1:500 and used for infecting the cells. In these conditions no reduction in viral replication was observed. These results suggested that resveratrol does not directly inactivate the viral particle. In a second phase, the cells were infected and treated with resveratrol, again using the same concentration (20 μg/ml), but the substance was added at various times after infection (0, 3, 6 and 9 h). Viral replication, assessed as HAU/ml 24 h after infection, revealed that this was significantly inhibited only if resveratrol was added within 3 h of infection (FIG. 4B). In contrast, if resveratrol, added immediately after infection, was removed at various times (0, 3, 6, 9 and 24 h), inhibition of replication was observed only if the treatment lasted for at least 9 hours. In addition, the results presented in FIG. 4 also show that the antiviral activity, once obtained, was not reversible on discontinuing the treatment.

Viral replication was also assessed with analysis of the occurrence of viral antigens on the surface of the infected cell by means of immunofluorescence. Analysis of viral proteins by immunofluorescence was done with a fluorescence microscope using a filter emitting in the green (FITC) (lens 100×). MDCK cells, cultured on cover slides for 24 h were infected and, 18 h after infection, were fixed with methanol-acetone 1:1 at 4° C. for 15 min. Later, the cells were washed twice in PBS and permeabilised with a 0.1% solution of PBS-TRITON for 5 min. Blockade of the aspecific sites was done with 1% milk dissolved in PBS for 30 min at ambient temperature. Later, specific monoclonal antibodies (mouse anti-influenza NP and mouse anti-influenza M) to viral proteins were added, diluted 1:50 in PBS for 30 min at ambient temperature. The primary antibody was detected with a secondary antibody conjugated to fluorescein (anti-mouse FITC, Sigma).

Figure 7:
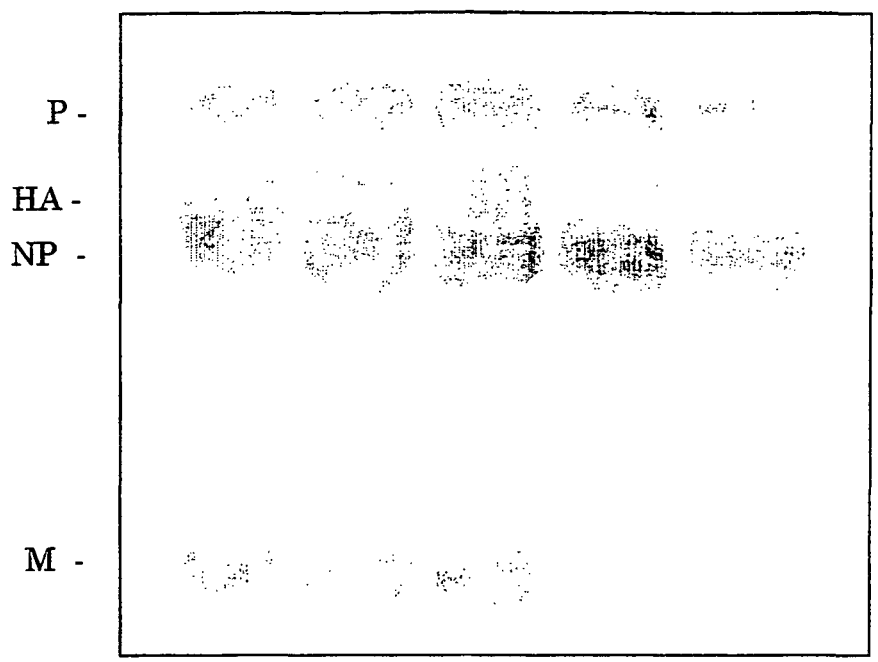
FIG. 7 illustrates the effect of resveratrol on the synthesis of viral proteins of the influenza virus PR8.
Figure 7:
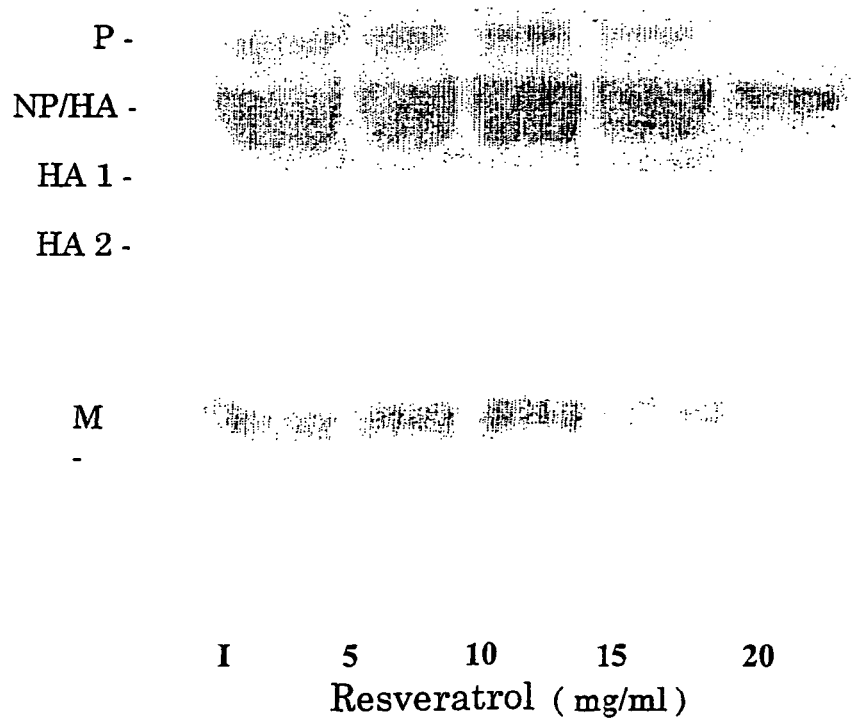

Analysis of Synthesis of Viral Droteins and Correlation with Antiviral Activity of Resveratrol Viral proteins were analysed by Western blotting. At different times after viral infection, the cells were lysed using special lysis buffers. Equal quantities of proteins were then loaded onto polyacrylamide gel in SDS. After electrophoresis, the proteins were transferred onto a nitrocellulose membrane and treated with anti-influenza polyclonal antibody. After incubation and suitable washings, the filters were treated with a second antibody conjugated to peroxidase and the viral proteins were highlighted by means of the chemiluminescence technique (ECL), using a peroxidase substrate (luminol) which, on reacting with the enzyme, emits a light and makes an impression on the autoradiography plate. The cells were treated with resveratrol at various concentrations (5, 10, 15 and 20 μg/ml). To allow better imaging of the viral proteins, the electrophoresis run was done using a 10% polyacrylamide gel (FIG. 7A) and gradient gel (FIG. 7B). Resveratrol at concentrations of 15 and 20 μg/ml almost totally inhibited the synthesis of the late influenza virus haemoagglutinin (H0-H1, H2) and matrix proteins (M). In contrast, the expression of early nucleocapside proteins (nucleoprotein [NP] and polymerase protein [P]) was inhibited, though to a lesser extent than that of the late proteins.

Analysis of the Synthesis of Messenger RNAs

For the purposes of identifying the mechanism of inhibition of viral proteins, MDCK cells, infected and treated with resveratrol at the different concentrations described above, were analysed by means of the PCR technique described by Tobita et al. (*J. Genteral Virol.*, 78, 563-566, 1997). MCDK cells infected with the virus and/or treated with resveratrol were homogenised with the reagent GIBCO BRL TRIZOL. After incubation at ambient temperature for 5 minutes, chloroform was added (0.2 ml per sample) and the samples were incubated at 15-30° C. for 3 minutes, Then, they were centiifuged at 10,000 rpm for 15 min at +4° C. and the aqueous phase containing the RNA was recovered. 0.5 ml of isopropanolol were added and the samples were incubated at 15-30° C. for 10 min and then centrifuged. The supernatants obtained were removed and the RNA precipitate was treated with 75% ethanol at 8,000 rpm for 5 min at 2-8° C. Lastly, the precipitate was air dried and dissolved in 20 μl of water-DEPC (diethyl pyrocarbonate).

The RNA obtained was transcribed using reverse transcriptase. The retrotranscription was done on 5 μl of RNA of each sample in a mixture consisting of random primers, the four deoxynucleotides (dNTP=cIATP, dCTP,dGTP, dTTP), dithiotreitol (DTT), and RT buffer (Life Technologies). The synthesis of complementary DNA (cDNA) was done by leaving the mixture for 10 min at 22° C., then for 60 min at 42° C. and finally the reaction was inactivated for 10 min at 75° C. The cDNA thus obtained was then used in PCR.

Taq polymerase was used in PCR. PCR was conducted in its three phases of denaturing, annealing and elongation at the respective temperatures of 95, 48 and 72° C. The cycle was repeated 20 times. The oligonucleotides used for the viral RNA amplification were: for the viral gene coding for the haemoagglutinin protein (HA) 5' primer: 5'-ACCAAAAT-GAAGGCAAACC-3', 3' primer: 5'-TTACTGTTA-GACGGG-TGAT-3'; for the viral gene coding for the matrix protein (M) 5' primer: 5'-ATGAGTCTTCTAACCG-3', 3' primer: 5'-ACTGCTTTGTCCATGT-3'. The PCR product was run in electrophoresis (100 volts) on a 1% agarose gel in a buffer in which ethidium bromide had been placed to display the DNA with a UV transilluminator.

Figure 8:
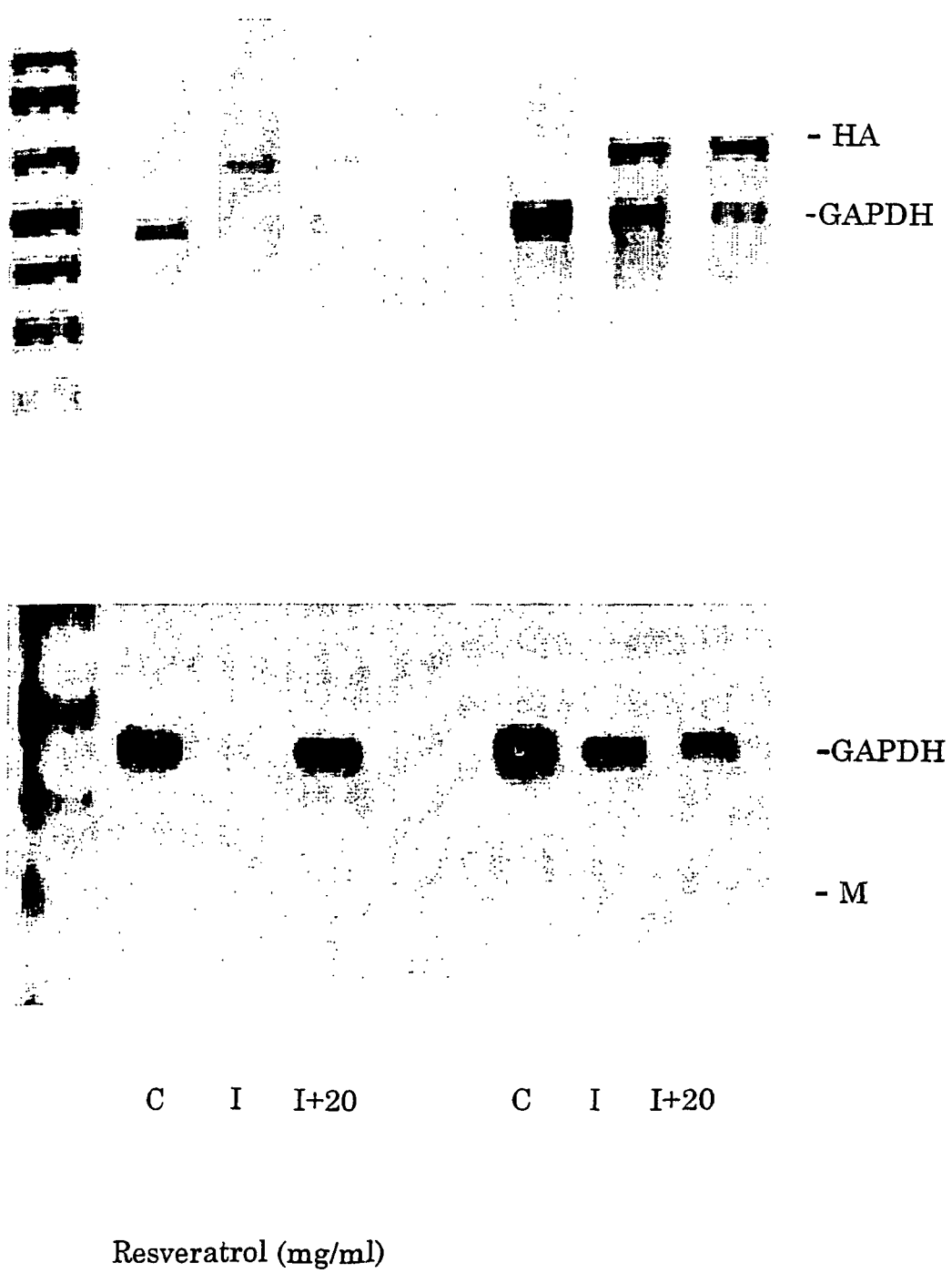
FIG. 8 illustrates the result of PCR for mRNA of late viral proteins.

The samples obtained were evaluated at 4, 8 and 20 h, respectively, after viral infection. Messenger RNAs for the viral proteins HA and M were not observed at 4 h either in the control or in the group treated with resveratrol. The results show that the synthesis of the mRNAs 20 h after infection is not affected by treatment with resveratrol. The observation at 4 h shows that resveratrol causes only a delay in messenger synthesis for these proteins (FIG. 8). These results suggest that reservatrol at doses of 20 μg/ml causes a delay in the release of messenger RNAs for the late viral proteins (HA and MV), evaluated 8 hours after infection.

Localisation of Protein NP

Considering that the inhibition of protein kinase C in cells infected by the influenza virus causes a substantial reduction in protein M expression, together with retention of the nucleoprotein of the nucleus of the infected cell (*J. Virol.*, 74, 1781-86, 2000), MDCK cells infected with the virus PR8 and treated or not with resveratrol at the concentration of 20 μg/ml were stained with specific anti-M and anti-NP antibodies and observed under the fluorescence microscope. The results revealed that, whereas in the uninfected cells NP is observed both in the nucleus and in the cytoplasm and M1 prevalently in the cytoplasm, in cells treated with resveratrol the NP is retained in the nucleus and M, which is significantly inhibited, can equally be observed only in the nucleus. This phenomenon may be attributable to inhibition of cell proteins with a kinase function. The data suggest then that the antiviral action mechanism may be related to the inhibition of proteins with a kinase function described above (*FEBS Letters*, 45, 63-7, 1999).

Assay of Reduced and Oxidised Alutathione

The glutathione assay has been performed as a result of the formation of S-carboxymethyl-derivatives of free thiols with iodoacetic acid followed by conversion of the $NH_2$ terminal groups to 2,4-dinitrophenyl derivatives after the reaction of 1-fluoro-2,4-dinitrobenzene (*Anal. Biochemn.*, 106, 55-62, 1980).

The MDCK cells were detached by means of the scraping technique. Later, the cells were centrifuged at 1,200 rpm for 5 minutes. The cells were washed twice in PBS and the precipitate, obtained after centrifuging, was resuspended in 200 µl of buffer. The cell lysates, obtained with repeated cycles of freezing and thawing, were deproteinised by means of precipitation in 5% metaphosphoric acid. After centrifuging at 22,300 g, the low-molecular-weight thiols present in the supernatant were derivatised with 10% iodoacetic acid v/v and neutralised with $NaHCO_3$ in powder form. After 1 h of incubation in the dark a solution of 1.5% 1-chloro-2,4-dinitrobenzene v/v was added (1.5 ml/98.5 ml of absolute ethanol). After adding the Sanger reagent, the samples were incubated for 12 h in the dark, and the separation of the various species of glutathione was done by means of a µBondapak 3.9×300 mm (Millipore) $NH_2$ HPLC column. To measure the total GSH content reference was made to a standard curve obtained with purified GSH. The GSH content is expressed in GSH nmol/mg proteins present in the lysate sample. The protein concentration was calculated using the Lowry method (*Biol. Chem.*, 193, 265-75, 1951). This method exploits the ability of proteins to reduce the Folin-Ciocalteau reagent in an alkaline solution with $Cu^{2+}$ ions, thanks to the presence of the phenol groups of a number of amino acids such as tryptophane, tyrosine, cysteine and histidine. Tryptophane and tyrosine react by means of their particularly reactive phenol groups, cysteine through the —SH group and histidine with the imidazole ring. The reducing reaction product is detected by the formation of stained compounds by reaction with the aromatic amino acids of the proteins. In fact, the solution takes on a particularly intense blue colour which has peak absorption at 695 nm. On the basis of the proportions of the absorption, the concentration of the proteins is therefore obtained in relation to a straight line calibration curve obtained using various concentrations of drum bovine albumin as the standard.

Figure 6:
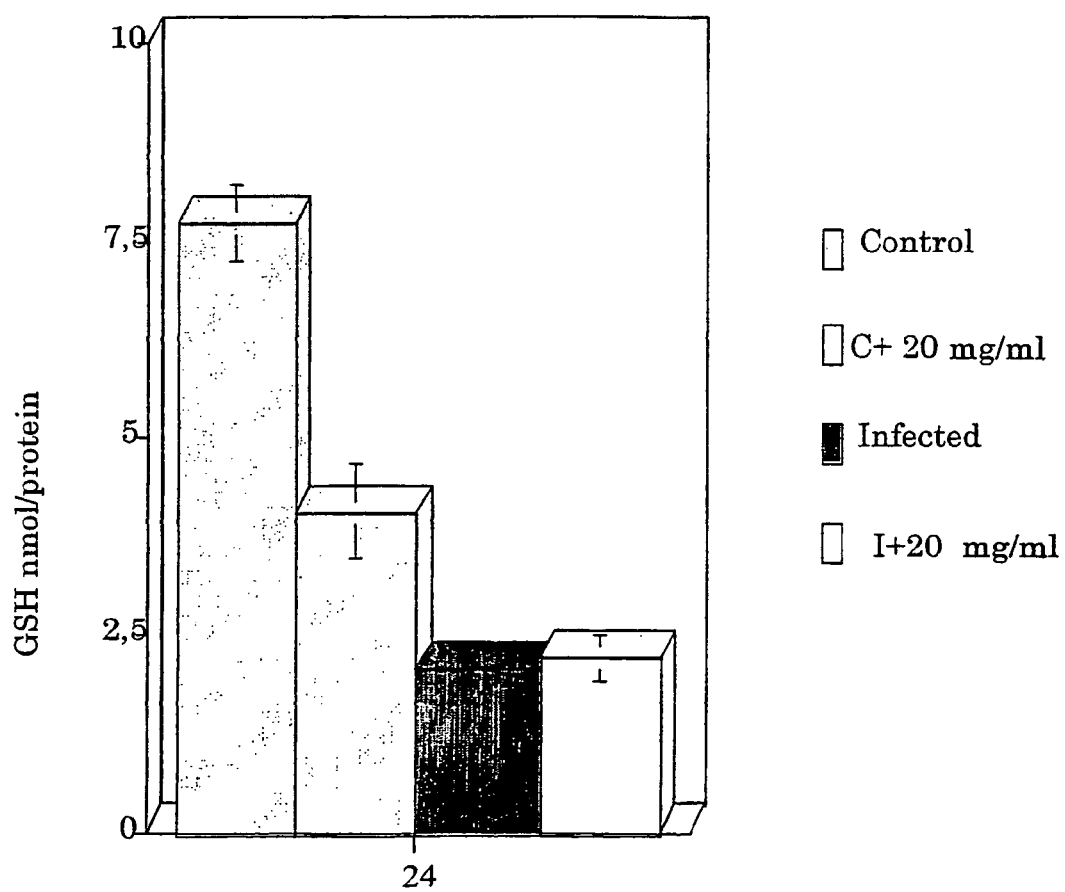
FIG. 6 illustrates the correlation between the antiviral effect of resveratrol and the intracellular redox state.

For the purposes of evaluating the possible correlation between antiviral activity and modulation of the redox state, the concentration of the cellular GSH of MDCK cells, treated with different reseivratrol concentrations and infected or not with the virus, was assessed by HPLC analysis 24 h after infection, Surprisingly, resveratrol added to uninfected MDCK cells produced a reduction in intracellular GSH levels as compared to untreated cells (FIG. 6). The addition of resveratrol to infected cells, though inhibiting viral replication, did not restore the GSH levels reduced by the infection.

Analysis of Apoitosis

As regards the analysis of apoptosis. MDCK cells were infected with the virus PR8. After viral adsorption, the cells were treated with resveratrol at various concentrations (5, 10, 15 and 20 µg/ml). Twenty-four hours after infection, the cells were detached using a 0.25% trypsin solution and then centrifuged at 1,200 rpm for 5 min, The precipitate thus obtained was analysed by means of the FACS technique after labelling with propidium iodide.

Figure 5:
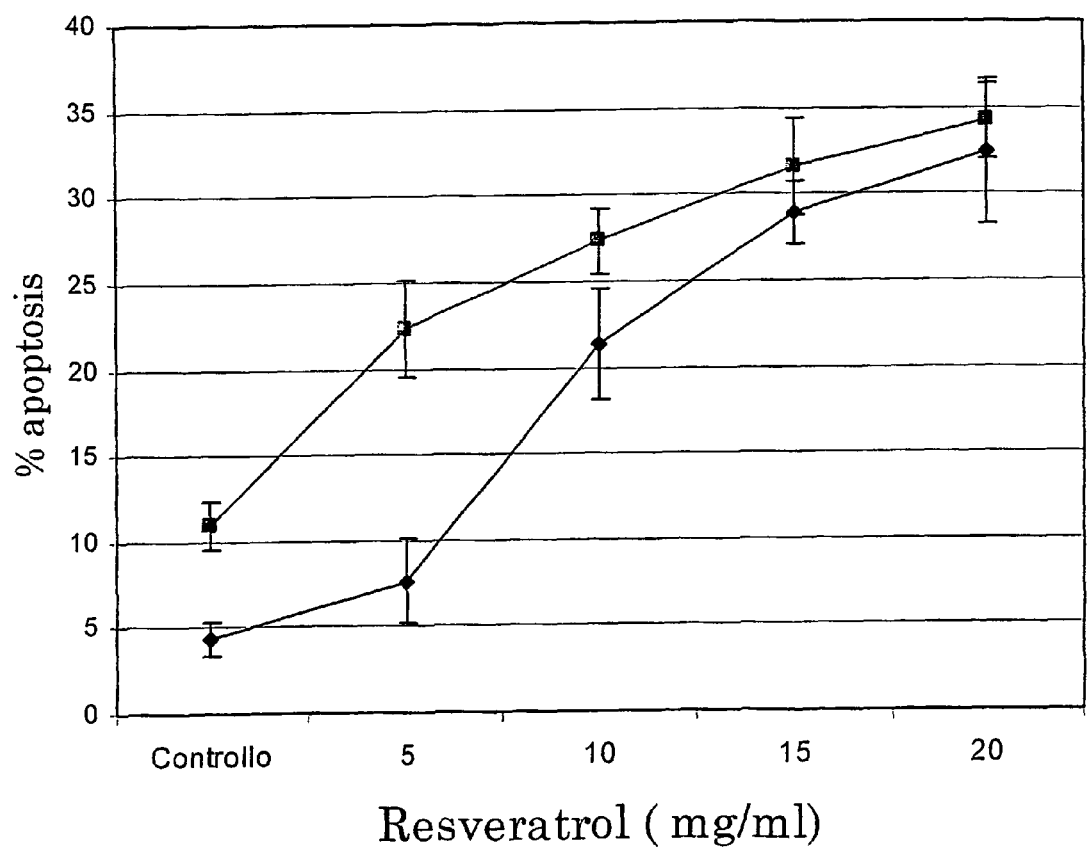
FIG. 5 illustrates apoptosis in MDCK cells treated with resveratrol (diamonds: not infected, squares: infected)

For the purposes of assessing whether the induction of cell death by apoptosis was involved in the antiviral effect of reservatrol, MDCK cells were infected or not with the virus and treated with the substance at the various concentrations. Cell death by apoptosis was evaluated by FACS after labelling with propidium iodide. As shown in FIG. 5, reservatrol caused a certain degree of cell death by apoptosis in uninfected cells ranging from 8 to 32% according to the doses (5 and 20 µg/ml, respectively). The infection in itself induced apoptosis in 12% of infected cells. Although the addition of increasing doses caused an increase in the mortality, no significant difference was observed between infected cells and uninfected cells treated with antiviral doses of the drug (35 and 37% apoptosis, respectively).

By way of further confirmation of the results of the present invention, and by way of examples, the following in-vivo studies are described.

EXAMPLE

Four-week-old female inbred Balb/c AnCrIBR mice were used. Resveratrol, dissolved in PBS, was administered to the animals via the intraperitoneal route at various times after infection with the influenza virus. The reservatrol concentrations were chosen so as to obtain a range of doses in the animals' blood similar to the effective range in vitro (10 to 20 µg/ml).

The mice were inoculated intranasally (i.n.) with a suspension containing the influenza virus A/PR at a multiplicity of infection of 2 HAU/mouse, after light anaesthesia with ether. On the basis of previous experimental data, the influenza virus at this multiplicity of infection produces haemorrhagic pneumonia that leads to the death of 80% of the animals by one week after infection. For the purposes of monitoring the infection trend, both virological and immunological parameters were monitored in addition to studying survival curves.

As a virological parameter, the viral load was determined. At different times after infection, the lungs of infected and control mice were taken as samples, weighed and homogenised in RPMI containing antibiotics. After centrifuging, the supernatants were suitably diluted and the viral load was analysed by means of the CPE-50% test. On the basis of this method, confluent MDCK cells were infected with the supernatants serially diluted in RPMI added with antibiotics at 2% FCS and incubated for three days at 37° C. in a 5% $CO_2$ atmosphere. Lastly. For each dilution, the wells showing positive effects were counted and compared with those showing negative cytopathic effects according to the Reed and Muench formula. The CPE-50% titre was calculated in units/ml.

As an immunological parameter, levels of inflammatory cytokines were evaluated using the ELISA method. A 96-well plate was used for the experiment. The plate was coated with monoclonal antibodies to the cytokines to be studied, incubated overnight at 4° C. Later, 200 µl/well of 1% BSA in carbonate buffer were added for 30 min at 37° C. Washings were then done with 0.25% TBS+Tween 20 and the samples were added for 4 hours at 37° C. As a reference curve recombinant cytokines in scalar dilution were used. Washings were then performed and an anti-cytokine polyclonal antibody, different from the first one, was added and left overnight at +4° C. Later, to washings with 0.5% TBS+Tween 20, $MgCl_2$ 2 nM was added the third antibody conjugated to the anzyme alkaline phosphatase for 4 h at 37° C. Lastly, a substrate for the enzyme (100 µl/well) was added and the readout was taken using the ELISA reader and a 405 nm filter. The following antibodies were analysed: 1) monoclonal rat anti-mouse TNF-alpha/recombinant mouse IL-6; 2) recombinant mouse TNF-alpha/recombinant mouse IL-6; 3) polyclonal rabbit anti-mouse TNF-alpha/polyclonal goat anti-mouse IL-6; 4) goat anti-rabbit IgG-alkaline phosphatase/anti-goat IgG alkaline phoshatase.

Figure 9:
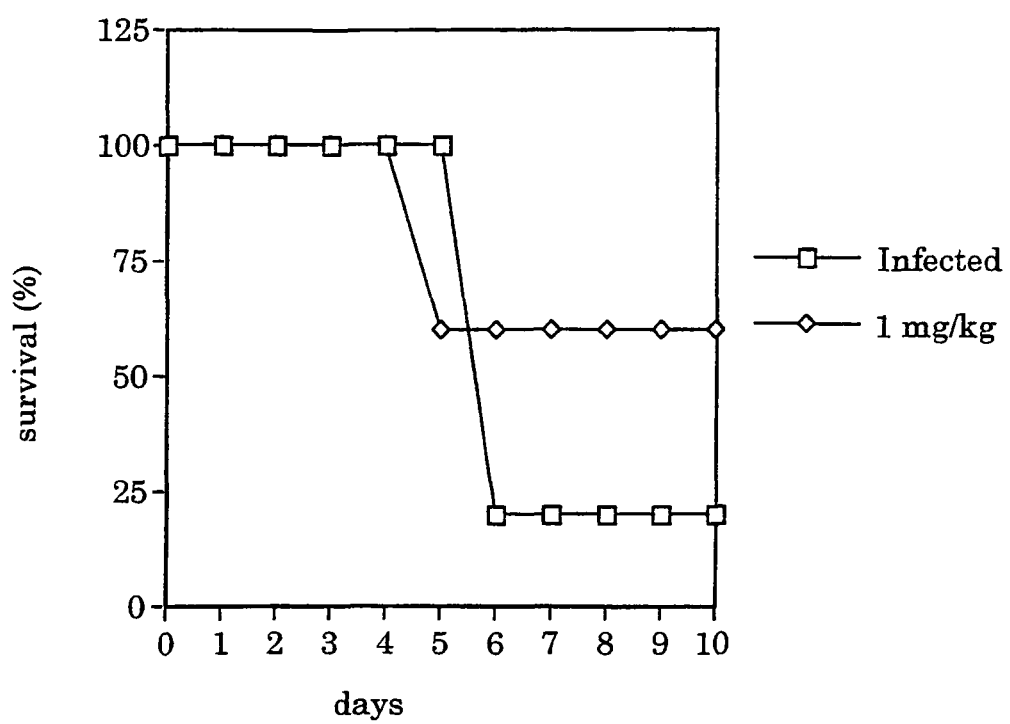
FIG. 9 illustrates the effect of resveratrol in vivo after infection with the influenza virus PR8.

The efficacy of resveratrol was studied in an experimental influenza virus infection model in the mouse. In this model, intranasal inoculation of the virus causes severe haemorrhagic pneumonia which leads to the death of the animals within 7 to 10 days of infection. The experimental design envisages evaluation of the therapeutic efficacy of the study substance, as assessed on the basis of survival of the infected animals. To this end, resveratrol was administered to the animals at various doses, on a daily basis for 7 days, starting from a few hours after infection. The results obtained show that, whereas the mortality of the untreated animals was as high as 80%, the administration of resveratrol (1 mg/kg) significantly reduced the mortality and 60% of the animals survived the infection (FIG. 9).

The invention claimed is:

1. A method of inhibiting influenza virus replication comprising administering to a subject having an influenza virus infection an amount of resveratrol which inhibits influenza virus replication and does not inhibit influenza virus target cell entry.

2. The method of claim 1 wherein the subject is a human and the influenza virus is human influenza virus.

3. The method of claim 1 wherein the influenza infection is a veterinary virus infection and the subject is a veterinary animal.

4. A method of treating an influenza virus infection comprising administering to a subject having an influenza infection an effective amount of resveratrol, which inhibits influenza virus replication and does not inhibit influenza virus target cell entry.

5. The method of claim 4 wherein the subject is a human and the influenza virus is human influenza virus.

6. The method of claim 4 wherein the influenza infection is a veterinary virus infection and the subject is a veterinary animal.

7. A method of non-reversibly inhibiting influenza virus replication comprising administering to a subject having an influenza infection an amount of resveratrol which inhibits influenza virus replication and does not inhibit influenza virus target cell entry.

8. The method of claim 7 wherein the subject is a human and the influenza virus is human influenza virus.

9. The method of claim 7 wherein the influenza infection is a veterinary virus infection and the subject is a veterinary animal.

10. A method of treating an influenza virus infection comprising administering to a subject having an influenza infection an effective amount of resveratrol which non-reversibly inhibits influenza virus replication and does not inhibit influenza virus target cell entry.

11. The method of claim 10 wherein the subject is a human and the influenza virus is human influenza virus.

12. The method of claim 10 wherein the influenza infection is a veterinary virus infection and the subject is a veterinary animal.

* * * * *